United States Patent [19]
Barner et al.

[11] Patent Number: 5,646,302
[45] Date of Patent: Jul. 8, 1997

[54] HETEROTRIFUNCTIONAL COMPOUNDS FOR PHOTOAFFINITY LABELLING

[75] Inventors: Richard Barner, Witterswil; Walter Huber, Kaiseraugst; Josef Hübscher, Nunningen; Jürg Hurst, Basel; Daniel Schlatter, Oberwil, all of Switzerland

[73] Assignee: Roche Diagnostic Systems, Inc., Branchburg, N.J.

[21] Appl. No.: 85,719

[22] Filed: Jun. 30, 1993

[30] Foreign Application Priority Data

Jul. 10, 1992 [CH] Switzerland ............... 2179/92

[51] Int. Cl.$^6$ .............. C07C 247/16; C07C 247/18; C07D 207/452
[52] U.S. Cl. .............. 548/542; 548/548; 546/294; 552/8
[58] Field of Search .............. 548/542, 548; 552/8; 546/294

[56] References Cited

U.S. PATENT DOCUMENTS 4,784,804  11/1988  Basch et al. ............... 552/8
4,784,805  11/1988  Blattner ............... 552/273
5,162,505  11/1992  Dean et al. ............... 530/391.5

OTHER PUBLICATIONS

Clement, et al., Biochemistry, 19:2196–2203 (1980) "Photoaffinity Labeling of Insulin Analogue Selectively Modified at the Amino Terminal of the B Chain".

Jung, et al., Biochimica et Biophysica Acta, 761:152–162 (1983) "Crosslinking of Platelet Glycoprotein by N-Succinimidyl".

Pele, et al., J. of Biol. Chem., 256:5064–5070 (1981) "A New Heterobifunctional Cross–linking Reagent for the Study of Biol. Interactions betw. Proteins".

Primary Examiner—Richard L. Raymond
Attorney, Agent, or Firm—George W. Johnston; Patricia S. Rocha-Tramaloni; Raina Semionow

[57] ABSTRACT

The invention is concerned with novel heterotrifunctional compounds which contain a chemically reactive group R, a photochemically reactive group Ar—N$^3$ and a reductively cleavable S—S(X$_2$)-group. The chemically reactive group and the photochemically reactive group are separated by a spacer group which contains a disulfide group. The water-solubilizing groups are carboxylic acids and sulfonic acids or derivatives thereof which are attached either to the aromatic ring or to the spacer group between the aromatic ring and the cleavable SS group. The compounds facilitate a novel photoaffinity method for the labelling of biomolecules, whereby the labelled biomolecule preserves its water solubility and the labelling molecule preferably projects free into the solution after anchorage to the surface of the biomolecule.

4 Claims, No Drawings

HETEROTRIFUNCTIONAL COMPOUNDS FOR PHOTOAFFINITY LABELLING

FIELD OF THE INVENTION

The present invention relates to the field of photoaffinity labelling. In particular, the present invention relates to a novel, heterotrifunctional compound and its use in a new photoaffinity labelling method for the planned chemical functionalization of biomolecules. This novel compound can also be used in conventional photoaffinity labelling methods.

DESCRIPTION OF RELATED ART

The methods described in the literature are generally carried out in a homogenous phase [Biochemistry, 1980, 19, 2196-2203; Biochimica et Biophysica Acta, 1983, 761, 152-162]. First, one of the partners of an affinity complex, such as an antigen in the labelling of antibodies or a ligand in the labelling of receptors, is reacted with the chemically reactive groups of the heterotrifunctional reagent. In the case of a large binding partner (e.g. protein-protein affinity complex), this partner of the affinity complex must react with several heterotrifunctional molecules in order to achieve an efficient affinity labelling. After this chemical modification of one of the binding partners, the affinity complex is formed by the addition of the second partner. Photolytic activation of the photoactivatable groups stabilizes this complex by covalent bond formation. Since these groups in the activated form are highly reactive groups which immediately re-react with their nearest neighbour, this bond formation takes place exclusively at or near the contact sites of the two partners of the affinity complex.

Subsequently, the affinity complex can be resolubilized by cleaving off the third functional group—the disulfide group—by reduction. The two partners can then be separated by suitably altering the pH value or the ionic strength. Both partners will contain free thiol groups, one with thiols arbitrarily distributed over the surface, the other partner with thiols localized on the regions in or near the binding site of the affinity complex. The two partners must then be separated in a subsequent separation step using known chromatographic techniques.

Several problems exist in current photoaffinity labelling methods. Photoaffinity labelling is preferably carried out in aqueous media in which the biomolecules to be labelled are not denatured. Therefore, photoaffinity labelling reagents must be water soluble. Many compounds presently used for functionalization are only moderately water soluble and require the addition of an organic solvent to maintain solubility in solution with the biomolecule.

In addition, during the labelling process the water-soluble portions of the reagents are cleaved off and the labelled biomolecules become water-insoluble. Further, the water-insoluble labels are deposited in the hydrophobic regions of the labelled molecules and are inaccessible for subsequent reactions.

The present invention addresses these problems.

SUMMARY OF THE INVENTION

The present invention relates to novel heterotrifunctional compounds for affinity labelling of biomolecules and to a novel method of photoaffinity labelling biomolecules on a solid phase surface resulting in chemical functionalization of the biomolecules.

The novel heterotrifunctional compounds in accordance with the present invention are compounds of the general formula:

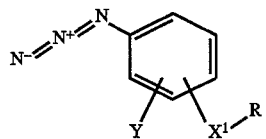

I wherein $X^1$ denotes a carbonyl (>C=O) or sulfonyl (>SO$_2$) and group Y=H,Y' or $X^1$—Y', group Y' is a hydroxy or alkoxy group (—O—Y") or an amino group (—NH—Y") in which Y"=H or a water-solubilizing group of the type (CH$_2$)$_n$A. n=1–6.

A is a glycol or oligoethylene glycol substituent or a tert. or quaternary amino group such as pyridyl, dialkylamino, N-alkylpyridinium or trialkylammonium. Alkyl denotes a lower alkyl residue, approximately $C_1$-$C_4$.

The group R is a functional group of the general formula:

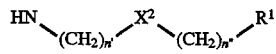

II wherein $X^2$ is a disulfide (—S—S—) or methylene group (—CH$_2$—).

$R^1$ denotes an amino (—NH—$R^2$) or carboxyl derivative (—CO—$R^3$). $R^2$=H or a derivatized carboxyalkanoyl group (—CO—(CH$_2$)$_n$CO—$R^3$).

CO—$R^3$ is an activated carboxyl group such as e.g. an acid halide, imidazolide, hydrazide, anhydride, a carboxyl group derivatized with a dithiopyridyl group (—NH—(CH$_2$)$_n$'"—S—S-pyridyl) or a reactive ester with e.g. hydroxysuccinimide, isourea or hydroxysuccinimidesulfonic acid.

n',n",n'"=1–6.

The present invention also relates to a novel method of photoaffinity labelling biomolecules which comprises covalently immobilizing the partner of the affinity complex which is selected for the planned labelling of a biomolecule to a solid phase, using a novel photoactivatable compound.

The object of the present invention is to provide compounds for the affinity labelling of biomolecules, which remain water-soluble throughout the labelling process thereby preserving the water solubility of the labelled biomolecules. The labelling molecules project freely into the solution after anchorage to the surface of the biomolecules.

An additional advantage in the use of these compounds is that the chromatographic separation required in known methods is eliminated.

DETAILED DESCRIPTION

The present invention relates to novel heterotrifunctional compounds for affinity labelling of biomolecules. It also relates to a novel method of photoaffinity labelling biomolecules on a solid phase surface resulting in chemical functionalization of the biomolecules.

The novel heterotrifunctional compounds in accordance with the present invention are compounds of the general formula:

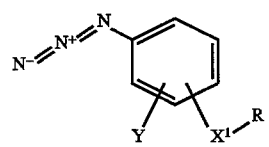

I wherein $X^1$ demotes a carbonyl (>C=O) or sulfonyl (>SO$_2$) and group Y=H,Y' or $X^1$—Y', group Y' is a hydroxy or alkoxy group (—O—Y") or an amino group (—NH—Y") in which Y"=H or a water-solubilizing group of the type (CH$_2$)$_n$A. n=1–6.

A is a glycol or oligoethylene glycol substituent or a tert. or quaternary amino group such as pyridyl, dialkylamino, N-alkylpyridinium or trialkylammonium. Alkyl denotes a lower alkyl residue, approximately $C_1$-$C_4$.

The group R is a functional group of the general formula:

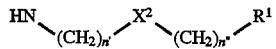
　　II wherein $X^2$ is a disulfide (—S—S—) or methylene group (—$CH_2$—).

$R^1$ denotes an amino (—NH—$R^2$) or carboxyl derivative (—CO—$R^3$). $R^2$=H or a derivatized carboxyalkanoyl group (—CO—$(CH_2)_n$CO—$R^3$).

CO—$R^3$ is an activated carboxyl group such as e.g. an acid halide, imidazolide, hydrazide, anhydride, a carboxyl group derivatized with a dithiopyridyl group (—NH—$(CH_2)_{n'''}$—S—S-pyridyl) or a reactive ester with e.g. hydroxysuccinimide, isourea or hydroxysuccinimidesulfonic acid.

$n', n'', n'''$ =1–6.

If $X^2$ denotes a methylene group, $R^3$ must contain a disulfide group, whereby $R^3$ denotes e.g. a cystamine derivative —NH—$(CH_2)_2$—S—S—$(CH_2)_2$—NH—$R^2$ wherein $R^2$ has the foregoing significance and the $R^3$ contained in $R^2$ does not contain a disulfide group.

When Y=H, $X^1$—R (without $R^3$) is hydrophilic (e.g. $X^1$=—$SO_2$— or $R^1$=tert.amine or quaternary ammonium).

For hydrophiles $X^1$—R (without $R^3$), Y can optionally also be $X^1$—R (double anchoring).

The amino group $R^1$ can also be converted into other reactive groups such as e.g. into an isocyanate, isothiocyanate, vinylsulfonamide (—NH—$SO_2$—CH=$CH_2$), maleimide, halo-substituted triazinamino, pyrimidinamino or pyridinamino compounds (e.g. dichlorotriazine), 2-halocarboxylic acid derivatives (e.g. with a 2-haloacetic acid halide, 2-halopropionic acid halide and the like), monoamides from dicarboxylic acid halides, epoxides, e.g. with epichlorohydrin or a cyclohexenedione derivative via Michael addition to a quinone.

```
X¹ = —CO—
X¹ = —SO₂—
X² = —S—S—
X² = —(CH₂)—
Y = —H                    A = —O—(CH₂)₂—O—H
Y = —Y'                   A = —O—[(CH₂)₂—O]ₙ—H
Y = —CO—Y' =              A = —N(alkyl)₂
 —X¹—Y' Y' =              A = —N⁺(alkyl)₃
 —O—Y" Y" = —H            A = -pyridine
Y = —SO₂—Y' =             A = -pyridinium(N-alkyl)
 —X¹—Y' Y' =
 —NH—Y'Y'=
 —(CH₂)ₙ—A R¹ = —CO—R³     R² = H          COR³ = CO—Cl
R¹ = —NH—R²     R² = —CO—       COR³ = CO—O-acyl
                (CH₂)ₙ—CO—R³    COR³ = CO-isourea
                                COR³ = CO—OSu
                                COR³ = CO—
                                 OSu(SO₃H)
                                COR³ = CO—NH—NH₂
                                COR³ = CO—NH—
                                 (CH₂)ₙ'''—
                                 S—S-pyridyl
                                COR³ = CO—NHCONH₂
                                COR³ = CO-imidazolyl
X₂ = —CH₂—,
```

$R^1$=$COR^3$=CO—NH—$(CH_2)_2$—S—S—$(CH_2)_2$—NH—$R^2$ ($R^2$=H, CO—$(CH_2)_n$—CO—$R^3$) in which $R^3$ is as defined in column 3 with the exception of the disulfide cpd.

$R^1$=pyridinium(N—$CH_2$—CO—$R^3$)

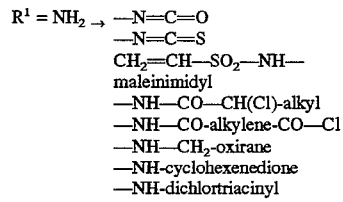

These novel compounds are heterotrifunctional because they contain a chemically reactive group R, a photochemically reactive group Ar—$N_3$ and a reductively cleavable —SS—($X^2$) group. The chemically reactive group and the photochemically reactive group are separated by a spacer group containing the cleavable —SS— group. Water-solubilizing groups comprise carboxylic acids or sulfonic acids or derivatives thereof which are attached either to the aromatic ring or to the spacer group between the aromatic ring and the cleavable —SS— group. This positioning guarantees that the water-solubilizing groups are incorporated with the label in the biomolecules to be labelled.

The present invention also relates to a novel method which introduces alkylthiol groups into biomolecules to be labelled (target biomolecules) while they are temporarily affixed to the surface of a solid phase in an intermediary outward-directed orientation. The partner of an affinity complex which recognizes a region of the target molecule, for example protein A for the labelling of Fc parts of antibodies, antigens or ligands for the labelling of antigen-binding or ligand-binding regions of antibodies or of receptors and vice-versa, or sDNA and DNA for the labelling of DNA-binding regions of DNA-binding proteins, is anchored onto the surface of a solid phase. The heterotrifunctional reagent is then bonded through its chemically reactive groups to the immobilized partner of the affinity complex. The target molecule is attached to the surface in an outwardly-directed orientation and bonded to the surface by activation of the photoreactive group.

Due to the special placement of the water-solubilizing groups on the phenyl ring or in the spacer group between the phenyl group and SS function in the heterotrifunctional reagent, the photochemically active region of the molecule projects into the aqueous phase after the reagent has been affixed to the surface. The probability of bonding between the water solubilizing groups of the reagent and the biomolecule is considerably increased due to the close proximity of the photoreactive groups to the regions of the biomolecule to be labelled and which have participated in the formation of the affinity complex. After reduction of the disulfide bond, for example with dithioeritrol, the labelled molecules can be washed off from the surface of the solid phase at a suitable pH value or ionic strength or with the addition of detergents.

The alkylthiol groups permit covalent anchoring of the biomolecules to corresponding functionalized surfaces and allow the attachment of additional groups, such as fluorophor groups, whereby not only the electrophilic character of the thiol group but also a thiol replacement can be used for such reactions. The alkyl moiety of the thiol functions as a spacer.

In an alternative embodiment, the photoactivatable reagent can be attached to the surface using a third molecule instead of the partner of the affinity complex. This third molecule can be immobilized on the surface of the solid phase before or simultaneously with the partner of the affinity complex to be immobilized. The advantage of incorporating such a labelled third molecule is that the covalently immobilized partner of the affinity complex is not labelled and therefore no loss of activity of this partner occurs. Using this labelling method, not only are the regions of the target molecule forming the affinity complex labelled, but all regions of the molecule which lie in the vicinity of the surface due to their orientation are also labelled.

Another advantage of the present invention is that labelling of certain types of biomolecules is possible without using the partner in an affinity complex. To support the orientation of these biomolecules, the surface of the solid phase can be prepared chemically so that a target molecule is adsorbed on this surface over a specific region. Examples of chemical preparation include preparing a membrane analogous surface for the labelling of a section in or near the transmembrane region of a membrane protein, or placing a metal complex on the surface with unsaturated coordination domains which are saturated by determined amino acid sequences of a protein for the labelling of the protein in the vicinity of the sequence. After orientation of the biomolecule on the solid phase surface, the heterotrifunctional compounds can also be reacted to the surface. The water-soluble photoreactive regions of these compounds project into the aqueous phase and react, after activation, with the superficially dose regions of the target molecule.

The following Example illustrates the production of the heterotrifunctional compounds:

41 mg of N-(p-azidobenzenesulfonyl) N'-(3-carboxypropionyl)cystamine were stirred for 5 hours with 1 ml of thionyl chloride and subsequently concentrated in a water-jet vacuum. The crude acid chloride was dissolved in 5 ml of THF and treated with 14 mg of N-hydroxysuccinimide as a solution in 1 ml of pyridine. The mixture was stirred for 2 hours and subsequently concentrated in a high vacuum. There were obtained 68 mg of N-(p-azidobenzenesulfonyl) N'-(3-succinimidyloxycarbonylpropionyl) cystamine as the pyridinium salt.

The starting material used was prepared as follows:

2.2 g of cystamine dihydrochloride were dissolved in 20 ml of water and adjusted to pH 10 with NaOH. 2.1 g of p-azidobenzenesulfonyl chloride were suspended in this solution and the suspension was stirred at room temperature for 5 hours. The precipitated N-(p-azidobenzenesulfonyl) cystamine was reacted with 2 g of succinic anhydride and stirred overnight. The resulting solution was acidified with HCl, subsequently filtered and washed with water. The residue was dried at room temperature in a high vacuum and gave 1.53 g of N-(p-azidobenzenesulfonyl) N'-(3-carboxypropionyl) cystamine. The IR showed bands at 3283 (amide NH) 2134 (azide), 1714 (acid carbonyl), 1650 (amide), 1589+1547 (aromatic), 1284 (COOH), 1328+1180 (arylsulfonyl ), 839 (p-disubst.benzene). TLC (silica gel—$NH_3$ conc./EtOH=1%) Rf=0.7. m.p.: dec. at 163°.

We claim:

1. A heterotrifunctional compound of the formula

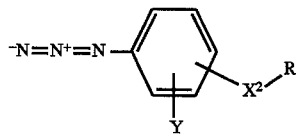

wherein $X^1$ is a sulfonyl group; Y is selected from the group consisting of hydrogen, Y' or $X^1Y'$; Y' is selected from the group consisting of a hydroxy group, an amino group and an alkoxy group; R is a functional group of the formula

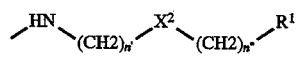

wherein $X^2$ is a disulfide or methylene group; $R^1$ is selected from the group consisting of an amino group (—NH—$R^2$); a reactive group selected from the group consisting of isocyanate, isothiocyanate, vinylsulfonamide (—NH—$SO_2$—CH=$CH_2$), maleimide, 2-halocarboxamides and monoamides from dicarboxylic acid dihalides; and a carboxyl derivative CO—$R^3$ selected from the group consisting of acid halide, hydrazide, anhydride a dithiopyridyl (—NH—$(CH_2)_{n'''}$—S—S— pyridyl), and a reactive ester with the group consisting of hydroxysuccinimide, isourea and hydroxysuccinimide-sulfonic acid; wherein when $X^2$ is a methylene group, $R^1$ must contain a disulfide group; $R^2$ is hydrogen or a derivatized carboxylalkanoyl group; and n', and n" and n''' are independently integers from 1–6.

2. The compound of claim 1, wherein the amino or alkoxy group or the group Y' is a group —NH—Y" or —OY" in which Y" is hydrogen or a group —$(CH_2)_nA$; A is a glycol or oligoethylene glycol substituent, a tert. or quaternary amino group selected from the group consisting of pyridyl, dialkylamino, N-alkylpyridinium and trialkylammonium; and n is an integer from 1–6.

3. The compound of claim 1, wherein Y is hydrogen, $X^2$ is a disulfide group, $R^1$ is an amino group —$NHR^2$, and $R^2$ is hydrogen or a derivatized carboxyalkanoyl group.

4. The heterotrifunctional compound of claim 3, N-(p-azido benzenesulfonyl)-N'-(3-succinimidyl oxycarbonyl propionyl) cystamine.

* * * * *

UNITED STATES PATENT AND TRADEMARK OFFICE
CERTIFICATE OF CORRECTION

PATENT NO. : 5,646,302
DATED : July 8, 1997
INVENTOR(S) : Richard Barner, Walter Huber, Josef Hübscher, Jürg Hurst, Daniell Schlatter It is certified that error appears in the above-indentified patent and that said Letters Patent is hereby corrected as shown below:

In claim 1, line 8, please replace Figure I with:

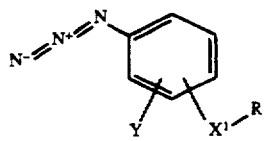   I

Signed and Sealed this

Thirtieth Day of September, 1997

*Attest:*

BRUCE LEHMAN

*Attesting Officer*   Commissioner of Patents and Trademarks